United States Patent [19]

LeFebre

[11] Patent Number: 5,184,193
[45] Date of Patent: Feb. 2, 1993

[54] DUAL FIBER OPTIC SPECTROPHOTOMETER

[75] Inventor: David A. LeFebre, El Dorado Hills, Calif.

[73] Assignee: Guided Wave, El Dorado Hills, Calif.

[21] Appl. No.: 293,218

[22] Filed: Jan. 4, 1989

[51] Int. Cl.$^5$ .......................... G01J 3/08; G01J 3/42; G02B 26/02
[52] U.S. Cl. .................... 356/325; 359/230; 356/328
[58] Field of Search .............. 356/319, 323, 324, 325, 356/328; 350/269; 359/230

[56] References Cited

U.S. PATENT DOCUMENTS

| | | | |
|---|---|---|---|
| 4,094,609 | 6/1978 | Fujii et al. | 356/210 |
| 4,285,596 | 8/1981 | Landa | 356/308 |
| 4,487,504 | 12/1984 | Goldsmith | 356/323 |
| 4,540,282 | 9/1985 | Landa et al. | 356/328 |
| 4,664,522 | 5/1987 | LeFebre | 356/334 X |
| 4,685,801 | 8/1987 | Minekane | 356/328 |
| 4,696,570 | 9/1987 | Joliot et al. | 356/319 |
| 4,786,171 | 11/1988 | LeFebre et al. | 356/326 |

FOREIGN PATENT DOCUMENTS

| | | | |
|---|---|---|---|
| 58-219435 | 12/1983 | Japan | 356/325 |
| 60-207019 | 10/1985 | Japan | 356/319 |
| 6514977 | 5/1966 | Netherlands | 356/323 |

OTHER PUBLICATIONS

Nassimbene "Light Shutter" IBM Tech. Disc. Bulletin, vol. 7 #1, Jun. 1964, p. 70.

Primary Examiner—Vincent P. McGraw
Attorney, Agent, or Firm—Poms, Smith, Lande & Rose

[57] ABSTRACT

Spectrophotometric apparatus and methodology suitable for continuous and long-term use. The apparatus includes a monochromator providing pre-dispersed monochromatic light to the optical inputs of a pair of fiber optic cables and a translator for alternatively positioning the fiber optic cables at the same location with respect to the monochromator output. One of the cables conducts light to a sample under study while the other cable provides a reference for light intensity measurements. The methodology includes the steps of performing two scans through the monochromator output for each measurement on the sample. The fiber optic cables are moved between scans so that the cable employed in the latter scan occupies the former position of the cable employed in prior scan.

51 Claims, 7 Drawing Sheets

DUAL FIBER OPTIC SPECTROPHOTOMETER

FIELD OF THE INVENTION

The present invention is generally directed to spectrophotometric apparatus for studying the optical properties of a sample and, more particularly, to spectrophotometric apparatus employing fiber optic waveguides for light transmission.

BACKGROUND OF THE INVENTION

Spectrophotometry concerns the study of the optical properties of a sample at various wavelengths. Typically, measurements are made of variations in the intensity of light either reflected from or transmitted through a sample as a function of wavelength. The resulting data can be used to determine the composition of the sample and the relative concentrations of the constituents making up the sample. This analysis is usually accomplished by comparing a spectral pattern of light intensities as a function of wavelength for the sample with the spectral patterns of known substances. The comparison process itself often involves complex mathematical techniques such as the use of Partial Least Squares With Latent Variables to match the spectral pattern of the known reference substances with the pattern of the sample.

Spectrophotometry has a wide variety of applications in both science and industry. In the latter usage, spectrophotometry has been used to determine the moisture and protein content of various grains and monitor product composition in flowing chemical production processes.

Spectrophotometers typically include a light source, a grating for dispersing light in a series of monochromatic, single wavelength, beams and some type of photodetector. The grating may be positioned to provide pre-dispersed monochromatic light to both the sample and the detector or, alternatively, polychromatic light from the source may be directed onto the sample and then dispersed by the grating before being directed to the detector. Since gratings commonly disperse light of varying wavelength at differing angles, the wavelength of the monochromatic light beam which eventually reaches the detector in either spectrophotometer configuration may be changed by simply rotating the grating. Fiber optic cables can also be employed to conduct light from the spectrophotometer to a distant sample. This approach has considerable advantages in industrial chemical processing applications.

Since spectrophotometric analysis depends upon a comparison of relative light intensities, it is desirable to maintain the intensity of light reaching the sample as uniformly constant as possible, both over the range of wavelengths being employed by the spectrophotometer and over the passage of time. The accuracy of a spectrophotometer is often characterized by the minimum intensity of light from the apparatus which fluctuates in a manner that cannot be otherwise compensated for.

One approach to enhancing the accuracy of a spectrophotometer is to maximize the uniformity of light produced within and conducted through the apparatus. Previous efforts have been made, for example, to develop a polychromatic light source having a highly uniform output. One example of this approach is illustrated in U.S. Pat. No. 4,094,609 to Y. Fujii, et al. Unfortunately, however, even the best light sources have discernible variations in light intensity at differing wavelengths which also change over time.

In addition to minimizing known sources of light intensity drift within a spectrophotometer, efforts have also been made to compensate for this drift by providing a reference spectral pattern which can be used analytically to account for variations in the light intensity of the sample spectral pattern which are not attributable to light interaction with the sample. In one application of this approach, illustrated in U.S. Pat. No. 4,696,570 to Joliot, et al., pre-dispersed monochromatic light from a grating is directed onto a fiber optic bundle which conducts the light to a sample. A small portion of the fiber optic bundle is also used to bypass the sample and conduct a fraction of the pre-dispersed monochromatic light onto a reference sample and then a detector. The spectral pattern from the reference sample is then used to compensate for variations in the intensity of the pre-dispersed monochromatic light beam entering the fiber optic bundle. This approach, however, still suffers from some inaccuracy.

In another application of the reference beam approach, illustrated in U.S. Pat. Nos. 4,285,596 and 4,540,282 to Lamda, et al., the sample under study is periodically replaced with a sample of known optical properties, such as teflon, to compensate for long term variations in light intensity as a function of wavelength. This approach requires a high degree of conformity in determining the wavelength at which a particular intensity measurement is made. The two Lamda, et al., patents are thus directed to grating drive systems suitable for repetitive determination of grating orientation in order to repetitively determine the wavelengths at which various light intensity measurements are made. In the former patent, a pair of complex configured cam members are employed, while in the latter patent, a two-pole brushless DC motor and flat return spring are used.

Periodically replacing a sample under study with a known reference material, however, can be inconvenient in a number of conventional spectrophotometric applications. In the case of flowing chemical production processes, for example, the flow of fluid under study must be blocked in order to provide an air reference sample. Thus the replacement process is typically time consuming and may also be labor intensive. Additionally, because of the speed of the grating drive system which is necessary to achieve a suitable repetitive accuracy, the duration and hence intensity of the light at any particular wavelength interacting with the sample may be undesirably low.

Thus there still exists a need for a spectrophotometric measurement apparatus and methodology which can provide enhanced accuracy. The present invention fulfills this need.

SUMMARY OF THE INVENTION

Briefly, and in general terms, the present invention provides a new spectrophotometer apparatus and measurement methodology with enhanced accuracy which is suitable for use in applications where the sample may be located at some distance from the spectrophotometric apparatus. Additionally, the spectrophotometer of the present invention may be used to simultaneously study the optical characteristics of several samples and can be operated for long periods of time with a high degree of repetitive accuracy.

More specifically, the present invention includes a spectrophotometric apparatus including a monochromator providing pre-dispersed monochromatic light at an output port, two separate fiber optic waveguides, one conducting light to a sample under study and the other providing a reference beam, and a translation apparatus for separately positioning the optical inputs of the two fiber optic waveguides at the monochromator output port. In use, the optical input of one of the fiber optic waveguides is positioned at the output port of the monochromator and the output from the monochromator is then scanned through a range of desired wavelengths while measurements of light intensity are made and stored. The translation device then replaces the optical input of the fiber optic waveguide with the optical input of the other waveguide, and the monochromator is scanned a second time through the desired range of wavelengths while light intensity measurements are again taken and stored. Variations in the spectral pattern of the sample which are not attributable to light interaction with the sample may then be minimized by analytically comparing the light intensity measurements at corresponding wavelengths taken during the two monochromator scans.

In one embodiment, the spectrophotometer of the present invention includes a third fiber optic waveguide for conducting light back from the sample and a photodetector optically coupled to both the reference beam fiber optic waveguide and the third or sample return waveguide. An optical multiplexer is also included to alternatively transmit light to the photodetector from either the reference waveguide or the sample return waveguide. In accordance with another aspect of this embodiment of the present invention, single strand fiber optic waveguides are employed in the spectrophotometer and several additional single strand waveguides are included so that light intensity measurements for several different samples may be taken during a single monochromator scan. A separate single strand fiber optic waveguide conducts light from the monochromator to each sample and an additional single strand waveguide is also associated with each of the sample waveguides to provide individual reference beams for each sample waveguide. The optical input ends of all of the sample and reference fiber optic waveguides are connected at the translation apparatus in a configuration which orients the optical endfaces of the sample waveguides in a single column with the reference waveguides oriented in an adjacent column so that corresponding sample and reference waveguides are positioned next to one another.

In an alternative embodiment, the spectrophotometer of the present invention includes a first photodetector optically coupled to the reference beam fiber optic waveguide and a second separate photodetector optically coupled to a fiber optic waveguide conducting light returned from the sample. This embodiment additionally permits simultaneous measurement of sample and reference light intensities so as to also compensate for short term fluctuations in light intensity at the monochromator output which occurred during the time required for a monochromator scan.

Another aspect of the present invention concerns a novel optical multiplexer for alternatively conducting light from two or more fiber optic waveguides. The multiplexer includes a base having several bores extending through the base and corresponding to the number of channels in the multiplexer. The opposing ends of each bore are configured to receive the end of a fiber optic waveguide with the waveguides projecting into the bore so as to leave a gap within the bore between the endfaces of the waveguides. An opaque ferromagnetic element is also disposed within the gap and electromagnets are connected to the multiplexer base so as to form separate magnetic fields of reversible polarity within each bore. Energizing the electromagnets so as to form a magnetic field of one polarity within the bore positions the ferromagnetic element within the gap so as to block the transmission of light between the endfaces of the ferromagnetic waveguides while producing a magnetic field of opposite polarity displaces the disk so as to permit light transmission. Where single strand fiber optic waveguides are employed, the waveguides preferably terminate in ferrules which are at least partially disposed within the bores of the multiplexer base with the single strand optical fibers displaced from a single longitudinal axis of the bores along a line generally parallel to the magnetic fields formed by the electromagnets.

Yet another aspect of the present invention concerns a monochromator having a rotatable grating and circuitry for determining the angular orientation of the grating with respect to an exit slit of the monochromator. This circuitry includes a precision linear potentiometer providing an output voltage signal proportional to the angular orientation of the grating, a control apparatus, such as a computer, for providing an output voltage signal corresponding to one of a series of predetermined grating orientations, a high gain differential amplifier having one input connected to the potentiometer and another input connected to the control apparatus and providing an output signal indicating a differential voltage between the two inputs, and a comparator, having an input connected to the output of the differential amplifier, providing an output signal whenever the output voltage signal from the differential amplifier is zero. This output signal from the comparator indicates when the angular orientation of the grating is equal to or closely approximates the predetermined grating orientation corresponding to the output voltage signal from the control apparatus, thus indicating the angular orientation of the monochromator with high precision.

Still another aspect of the present invention concerns circuitry for measuring the output voltages of the photodetectors sensing the light intensity from the reference and sample light beams and providing an output signal suitable for use by a control computer. This circuitry includes a sample and hold device connected to the output of the photodetector, which holds the output voltage from the detector upon receipt of a command signal, a programmable amplifier connected to the output of the sample and hold device for providing amplification of variable magnitude to the voltage level output of the sample and hold device and a second sample and hold device connected to the output of the programmable amplifier. In use, a command signal is sent to the first sample and hold device to store the voltage output of the photodetector when light of a desired wavelength is conducted to the photodetector through the spectrophotometer. The programmable amplifier then provides to the second sample and hold device an amplified form of the voltage stored in the first sample and hold device, with the computer accessing the voltage stored in the second sample and hold device through a suitable analog to digital converter. The control signal to the first sample and hold device may be provided from the computer or, alternatively, from the output of the monochromator comparator discussed above. The computer can also be used to control the amplification of the programmable amplifier so as to optimize the range of voltages stored in the second sample and hold device to within a desired dynamic range of the analog to digital converter which provides maximum accuracy.

In an alternative embodiment, several sample and hold devices are connected to the output of the photodetector and an electrical multiplexer is combined with the programmable amplifier so that the output voltage of the photodetector may be simultaneously stored in several sample and hold circuits and subsequently measured, thus minimizing variations in signal intensity attributable to the photodetector and the voltage measuring circuitry.

The novel features which are believed to be characteristic of the present invention will be better understood from the following detailed description, considered in connection with the accompanying drawings, wherein like numbers designate like elements. It should be expressly understood, however, that the drawings are for purposes of illustration and description only and are not intended as a definition of the limits of the present invention.

BRIEF DESCRIPTION OF THE DRAWINGS

FIG. 12 is a perspective view of one embodiment of a spectrophotometer according to the invention with a front cover panel opened for convenience of illustration.

Figure 1:
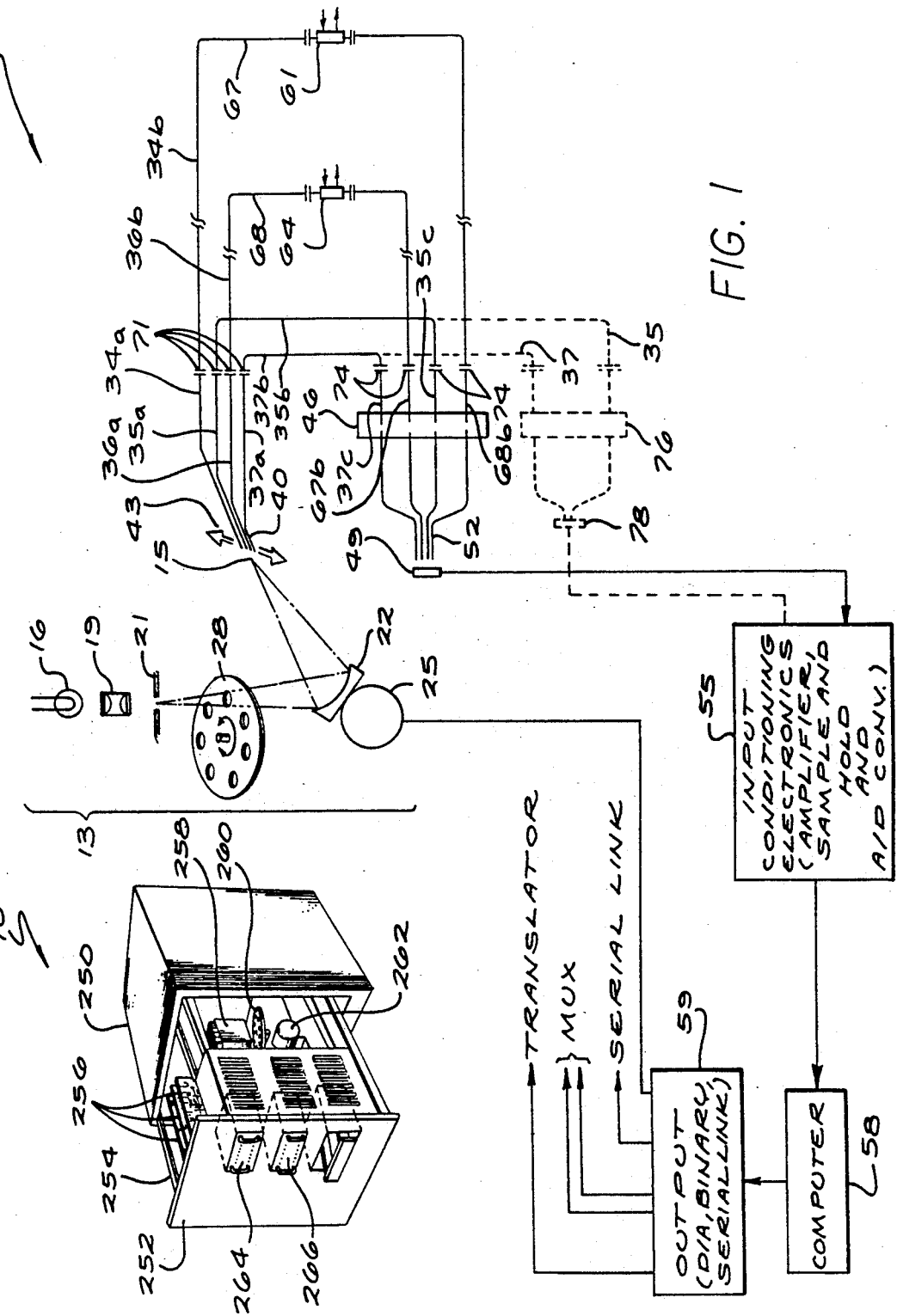
FIG. 1 is a representational schematic of the spectrophotometer of the present invention.

DETAILED DESCRIPTION OF THE INVENTION:

Referring to the figures, and more particularly FIG. 1, there is shown a schematic representation of an illustrative embodiment of the spectrophotometer 10 of the present invention. The spectrophotometer 10 includes a monochromator 13 providing pre-dispersed monochromatic light at an exit aperture 15. The monochromator 13 includes a light source 16, focusing optics 19 and entrance slit 21 to direct a polychromatic light beam onto a grating 22. The light source 16 can be of any suitable type such as a tungsten lamp, and the focusing optics 19 can similarly be of any suitable type known in the art for having a minimum variation in focus at different wavelengths. The grating 22 is preferably a concave holographic grating, the lines of which have been formed by holographic techniques. Gratings of this type typically have aberration corrections, providing high light energy throughput. The monochromator 13 also includes a grating drive 25 for rotating the grating 22 and measuring the angular orientation of the grating 22 with respect to the exit aperture 15, and a filter wheel 28 for modulating the output of the monochromator 13 and also calibrating the grating drive 25.

The spectrophotometer 10 further includes two complementary pairs of light conducting fiber optic cables 34, 35 and 36, 37. As discussed more fully below, the optical inputs 40 of the fiber optic cables 34–37 are joined together and connected to a translation apparatus 43 which reciprocally positions the optical inputs 40 of the fiber optic cables 34–37 so that the optical inputs of each of the fiber optic cables 34 and 35 can occupy the same position with respect to the monochromator exit aperture 15 and so that the optical inputs of each of the fiber optic cables 36 and 37 can similarly occupy the same position with respect to the exit aperture 15. In the presently preferred embodiment, the fiber optic cables 34–37 are preferably single strand optical fiber waveguides. Fiber optic cables of this sort are known in the art, one source of suitable single strand fiber optic cable is Guided Wave, Inc., located in Eldorado Hills, Calif. In the preferred embodiment, fiber optic cables disposed within the spectrophotometer 10 are provided with a polyimide coating while fiber optic cables used outside the spectrophotometer 10, as discussed more fully below, are further jacketed with a layer of silicone followed by a tight tube extrusion, braid and a final extruded jacket.

The spectrophotometer 10 also includes an optical multiplexer 46 having four channels for alternatively transmitting light conducted through the fiber optic cables 34–37 to a photodetector 49. The multiplexer 46 is optically coupled to the detector 49 by four fiber optic cables 52. Each fiber optic cable 52 is connected at one end to a separate output of the optical channels of the multiplexer 46 and individually connected at another end to an active portion of the detector 49. Conditioning electronics 55 are also provided for measuring the output of the detector 49 and providing suitable digitized signals to a computer 58 controlling the operation of the spectrophotometer 10.

For illustrative purposes, the spectrophotometer 10 illustrated in FIG. 1 is configured to study the optical properties of two separate samples respectively disposed within sample chambers 61 and 64. The sample chambers 61 and 64 may be of any conventional form known within the spectrophotometric art. One type of sample chamber, particularly suitable for use in analyzing the composition of flowing fluids, is disclosed in U.S. Pat. No. 4,786,171 to LeFebre, et al. It should be expressly understood, however, that for the purposes of the present invention the spectrophotometer 10 could also be configured to study several additional samples, or only one sample, simply by changing the number of pairs of fiber optic cables within the spectrophotometer 10 and the number of optical channels in the multiplexer 46. One embodiment of the present invention has been developed for studying the optical properties of up to four separate samples.

As discussed more fully below, the fiber optic cables 34 and 36 of the fiber optic cable pairs 34, 35 and 36, 37 are used as sample cables and conduct light from the monochromator 13 to the sample chambers 61 and 64. Additional fiber optic cables 67 and 68 return light from the sample chambers 61 and 64 to the multiplexer 46. The other fiber optic cables 35 and 37 are used as reference cables and conduct light from the monochromator 13 directly to the multiplexer 46. In this illustrative embodiment, the relatively stable and low optical attenuation characteristics of fiber optic cables are also advantageously employed to locate the sample chambers 61 and 64 distant from the spectrophotometer 10. Optical interconnects 71 and 74 which facilitate the transmission of light between separate fiber optic cables are provided to respectively divide the sample fiber optic cables 34 and 36 and the return cables 67 and 68 into separate sets of fiber optic cables 34a, 36a and 67a, 68a disposed within the spectrophotometer 10 and into separate sets of fiber optic cables 34b, 36b and 67b, 68b disposed outside the spectrophotometer 10. The reference fiber optic cables 35 and 37 are similarly preferably divided into fiber optic cables 35a and 37a extending from the monochromator exit aperture 15 to the optical interconnect 71, fiber optic cables 35b and 37b disposed outside the spectrophotometer 10 and fiber optic cables 35c and 37c within the spectrophotometer 10 between the optical interconnects 74 and the multiplexer 46.

In operation of the spectrophotometer 10, the grating drive 25 is first calibrated so that output signals from the grating drive 25 can be correlated to the wavelength of the monochromatic light produced at the exit aperture 15 of the monochromator 13. This correlation process is carried out for each pair of reference and sample fiber optic cables 34, 35 and 36, 37. The filter wheel 28 is first rotated to a calibration filter which transmits light at two or more known wavelengths. The grating is then scanned through its operational range of angular orientations, thus scanning the wavelength of monochromatic light produced at the exit aperture 15. The outputs of the detector 49 and the grating drive 25 are monitored by the control computer 58 during this scan. When peak signals are sensed by the detector 49, corresponding to the transmission of light having a known wavelength through the calibration filter of the wheel 28 and thus indicating that the grating 22 is oriented to reflect this wavelength to the monochromator exit aperture 15, the output signal of the grating drive 25 is recorded. Utilizing the output signals from the grating drive 25 which are generated when at least two known wavelengths are sensed by the detector 49, a relationship can be calculated for the entire operational range of the monochromator that correlates signals from the grating drive 25 with the wavelengths of the light output from the monochromator 13. In one presently preferred embodiment, the range of the monochromator is divided into more than two thousand steps, each representing a single wavelength of light output from the monochromator 13. With the dynamic range of the presently preferred embodiment of the monochromator 13, each of these steps represents a change of less than one nanometer in the wavelength of the monochromatic light produced at the exit aperture 15.

In the case of the illustrative spectrophotometer 10 illustrated in FIG. 1, four sets of initial light intensity measurements are taken after the grating drive 25 is calibrated. These light intensity measurements correspond to the transmission of light through each of the different optical paths through the fiber optic cables 34–37. Thus, for example, for each complementary pair of fiber optic cables 34, 35 and 36, 37, a set of light intensity measurements $I_{sr}(\lambda)$ and $I_{rr}(\lambda)$ are taken. The first subscript in each of the terms $I_{sr}$ and $I_{rr}$ designates the optical path to the detector as being through either the sample or reference fiber optic cable while the second subscript indicates that the measurements were recorded during an initial reference scan.

In order to perform the initial light intensity measurements, the computer 58 directs the optical multiplexer 46 to separately transmit light through one of its optical channels to which the fiber optic cables 35c, 37c, 67b and 68b are connected while the light output of the monochromator is scanned through its desired operational range of wavelengths. Thus, for an entire scan, light is conducted through only one optical channel. During these initial scans, the sample chambers 61 and 64 are empty. Additionally, the translator 43 reciprocally positions the respective optical inputs of the fiber optic cables 34–37 so that the individual optical inputs of the fiber optic cables within the respective complementary fiber optic pairs 34, 35 and 36, 37 occupy the same location with respect to the monochromator exit aperture 15 during the respective scans. Thus during a first scan the sample fibers 34 and 36 of the complementary paris of sample and reference fibers 34, 35 and 36, 37 would occupy a particular location with respect to the monochromator exit aperture 15 while during a second scan, the reference fibers 35 and 37 would occupy that same location.

When a spectrophotometric analysis of a sample is to be performed, the light output of the monochromator again scans through its range of wavelengths a separate time for each of the optical paths through the fiber optic cables 34–37 and measurements of light intensity are taken. As with the initial set of reference scans, the translator 43 positions the optical inputs 40 of the fiber optic cables 34–37 so that the optical inputs of the individual fiber optic cables within the respective complementary fiber optic cable pairs 34, 35 and 36, 37 occupy the same location with respect to the monochromator exit aperture 15 during their respective scans. Thus, for each measurement of a sample, two scans occur.

By way of illustration, when a sample within the chamber 61 is to be studied, the translator 43 positions the optical input 40 of the sample fiber optic cable 34 at the monochromator exit aperture 15 and a set of light intensity measurements $I_{ss}(\lambda)$ are taken as the light output of the monochromator is scanned. In this term, $I_{ss}(\lambda)$, the first subscript s indicates measurement through the sample fiber optic cable 34 and the second subscript s indicates that the monochromator scan occurred during a sampling period. The translator 43 then positions the optical input 40 of the reference fiber optic cable 35 at the same physical location previously occupied by the optical input of the sample fiber optic cable 34 and a second set of light intensity measurements $I_{rs}(\lambda)$ are performed. Similarly, the optical input of the reference fiber optical cable 37 will now occupy the physical location previously occupied by the optical input of the sample fiber optic cable 36. In the term, $I_{rs}(\lambda)$, the first subscript r denotes measurements taken through the reference fiber optic cable and the second subscript indicates that the scan occurred during the sampling period.

Long term compensation for drift in the light intensity output of the monochromator 13 can then be compensated by correcting the set of light intensity measurements taken during the sampling scan through the following equation:

$$A(\lambda) = \log\left[\left(\frac{I_{SR}}{I_{SS}}\right)\left(\frac{I_{RS}}{I_{RR}}\right)\right]$$

The above procedure provides stable operation of the spectrophotometer 10 for periods of time which can extend over tens of days, with unaccountable drift in the corrected light intensity measurements of less than 500 micro AU, peak to peak, over a broad range of spectral wavelengths.

Variations in the intensity of the light output from the monochromator that occur within the time duration of a scan, typically three seconds, cannot be compensated for by this approach. An alternative illustrative embodiment of the spectrophotometer 10 of the present invention is therefore shown in dashed lines in FIG. 1 which can be used to partially compensate for those light intensity variations occurring within the course of a scan. In general terms, the procedure discussed above is modified by simultaneously measuring light intensities conducted through both the reference and the sample fibers of each complementary fiber optic cable pair during the course of a single sample and reference scan. Accordingly, the spectrophotometer 10 is modified by directing the optical path through the reference fiber optic cables 35 and 37 to a separate optical multiplexer 76 which is optically coupled to a separate additional detector 78. The sampling procedure discussed above is then modified by taking a third additional set of light intensity measurements. These measurements are taken from the reference fiber optic cable during the same time that light intensity measurements are taken from the sampling fiber optic cables 34 and 36. Both long and short term variations in the light intensity output of the monochromator are then compensated for by the following equation:

$$A(\lambda) = \log\left[\left(\frac{I_{SR}}{I_{SS}}\right)\left(\frac{I_{RS}}{I_{RR}}\right)\left(\frac{I_{RSD}}{I_{RRD}}\right)\right]$$

The third subscript in the new term of the above equation is employed to indicate that these light intensity measurements are taken while the reference fiber optic cable is displaced from its normal scan position with respect to the monochromator exit aperture 15. This displacement is necessary since that location is occupied during this scan by the optical input of the sampling optical fiber cable. The degree of simultaneous compensation is related to spatial anomalies at the monochromator exit aperture 15 and approaches or exceeds about eighty percent of the variation.

Figure 2:
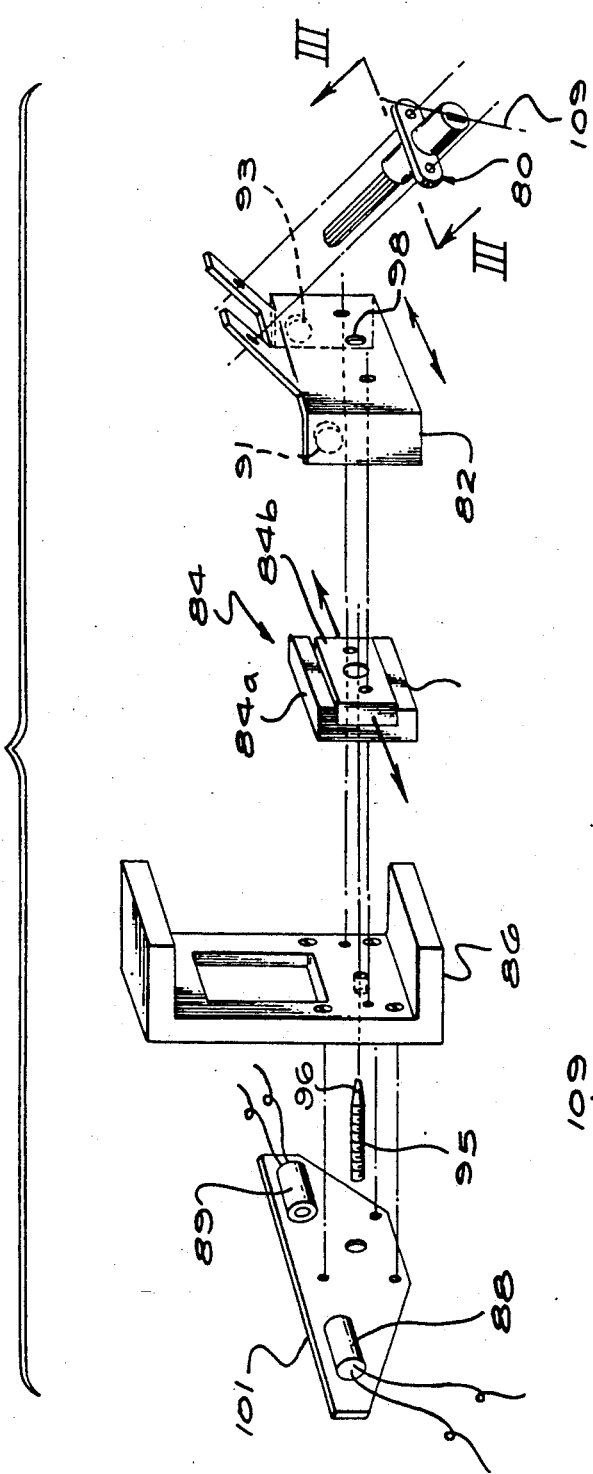
FIG. 2 is an exploded perspective view of the fiber optic translation device of the present invention.

Referring now to FIG. 2 there is shown an embodiment of the translation device 43 diagrammatically illustrated in FIG. The translator 43 includes a ferrule 80 securing the optical inputs of the fiber optic cables 34-37 shown in FIG. 1. The ferrule 80 is secured to a bracket 82 which is in turn connected to a translation stage 84. The stage 84 includes two portions 84a and 84b which can move with respect to one another along a single axis. Suitable translation stages are well known in the art and are available from various manufacturers of optical equipment. As illustrated in FIG. 2, one portion 84a of the translation stage 84 is mounted to a base member 86, while the bracket 82, securing the ferrule 80 is mounted to the other portion 84b of the translation stage 80.

To effect relative movement of the translation stage portions 84a and 84b, two electromagnets 88 and 89 are mounted onto a support plate 101, which is in turn bolted to the base 86. The electromagnets 88, 89 alternatively attract a pair of permanent magnets 91 and 93 connected to the interior surfaces of the bracket 82. Thus, in use, the electromagnets 88 and 89 can be alternatively energized so that, for example, electromagnet 88 attracts the permanent magnet 91, thus moving the stage portion 86b toward the electromagnet 88. Alternatively, the electromagnet 89 may be energized so as to attract the permanent magnet 93, thus displacing the stage portion s toward the electromagnet 89.

The travel distance of the stage portion 86b is limited by a lead screw 95, threaded into the base 86, and having a conic tip 96 which engages the edges of an aperture 98 in the bracket 82. Threading the lead screw 95 into and out of the base 86 thus varies the travel of the stage 84.

Figure 3:
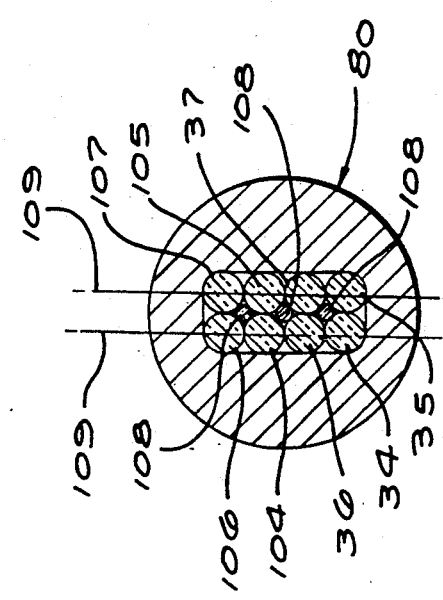
FIG. 3 is an end view of the optical inputs for the sample and reference fiber optic cables of the spectrophotometer of the present invention.
Figure 4:
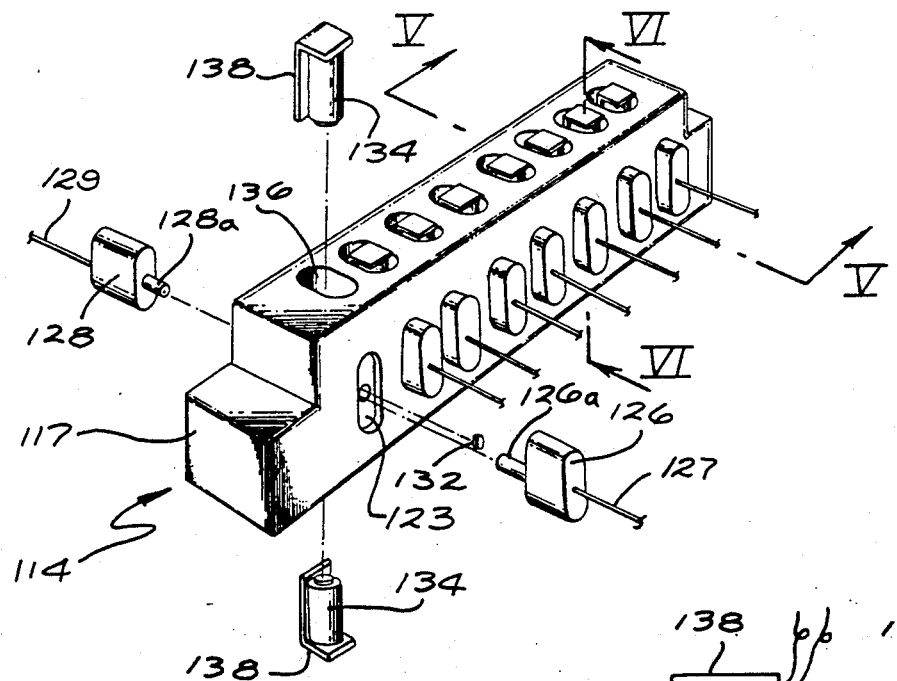
FIG. 4 is an exploded perspective view of the optical multiplexer of the present invention.

Referring to FIG. 3, there is shown the endface of the ferrule 80 securing the optical inputs 40 of the fiber optic cables 34-37. For illustrative purposes, however, four additional fiber optic cable endfaces 104, 105, 106 and 107 are shown. These additional fiber optic cables form two additional complementary fiber optic cable pairs 104, 105, 106, and 107 which could be used in connection with two additional sample chambers (not shown) with the fiber optic cables 104 and 106 acting as sample fibers and conducting light to the sample chambers and with the fiber optic cables 105 and 107 acting as reference fibers, bypassing the sample cells and conducting light directly to the optical multiplexer 46.

As illustrated, the complementary fiber optic cable pairs 34, 35, 36, and 37 as well as the complementary pairs 104, 105, 106, and 107 are disposed adjacent one another in the ferrule 80 so as to form two parallel columns of sample fiber optic cables and reference fiber optic cables. Thus, the sample fiber optic cables 33, 36, 104 and 106 form a sample column while the reference fiber optic cables 35, 37, 105 and 107 form a reference column.

In the preferred embodiments of the present invention, the fiber optic cables 34-37 and 104-107 are single-strand fiber optic waveguides. The ferrule 80 is formed by bonding the individual, single-strand fiber optic cables together under pressure and then forming a curable plastic structure about the ends of the bonded fiber optic cable columns. Smaller diameter fibers 108 are preferably disposed in the intertesties between the sample and the reference columns to aid alignment of the columns during their fabrication. The endface of the ferrule 80 is then polished to a finish sufficient for optical transmission through the single-strand fiber optic cables. This fabrication process provides that all of the single-strand fiber optic cables will have virtually identical finishes and polishing angle biases.

The ferrule 80 is attached to the translator bracket 82 that the longitudinal axis 109 of the sample column of fiber optic cables 34, 36, 104 and 106 and the reference column of fiber optic cables 35, 37, 105 and 107 are oriented perpendicular to the axis of relative travel between the stage portions 84a, 84b. The translator 43 is then mounted relative to the monochromator exit aperture 15 so that the travel axis of the stage portions 84a, 84b is oriented parallel to the rotational axis of the grating. This orientation of the column of fiber optic cables 34, 36, 104 and 106 and the column of fiber optic cables 35, 37, 105 and 107 permits simultaneous sensing of the light intensities conducted through both of the fiber optic cables in each of the complimentary pairs of fibers during a single sampling scan and further minimizes inaccuracies between scans in a single sampling.

Referring to FIGS. 4–8, a long life, high through-put and fast response optical multiplexer 114 is shown that is suitable for use as the optical multiplexer 6 of the spectrophotometer 10 illustrated in FIG. 1. The multiplexer 114 includes a base 117 having a series of bores 118 extending through the base 117 for conducting light through the multiplexer 114. Each of the bores 118 represents a separate optical channel of the multiplexer 114. In this embodiment, the base 117 is provided with a series of depressions 123 generally disposed about the bores 118. Both the bores 118 and the depressions 123 are configured to tightly receive ferrules 126 which terminate the input fiber optic cables 127 and ferrules 128 which terminate the output fiber optic cables 129. The ferrules 126 and 128 respectively contain cylindrical portions 126a and 128a configured to project into the opposing ends of the bores 118 so as to leave a small gap between the endfaces of the opposing ferrules. A small opaque ferromagnetic element 132 is disposed within the gap inside each bore 118. Optical switching is accomplished in each channel of the multiplexer 114 by displacing the element 132 with magnetic fields generated by electromagnets 134 disposed within cavities 136 formed in opposing sides of the base 117 perpendicular to and adjacent each of the bores 118.

Figure 8:
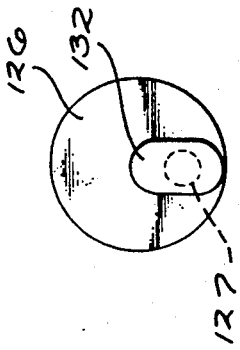
FIG. 8 is an end view of the optical transmission gap in the optical multiplexer of the present invention, illustrating a closed optical channel.
Figure 7:
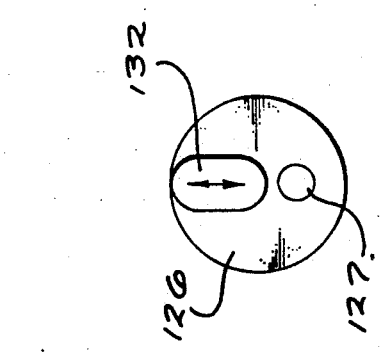
FIG. 7 is an end view of the optical transmission gap within the optical multiplexer of the present invention, illustrating an open optical channel.
Figure 5:
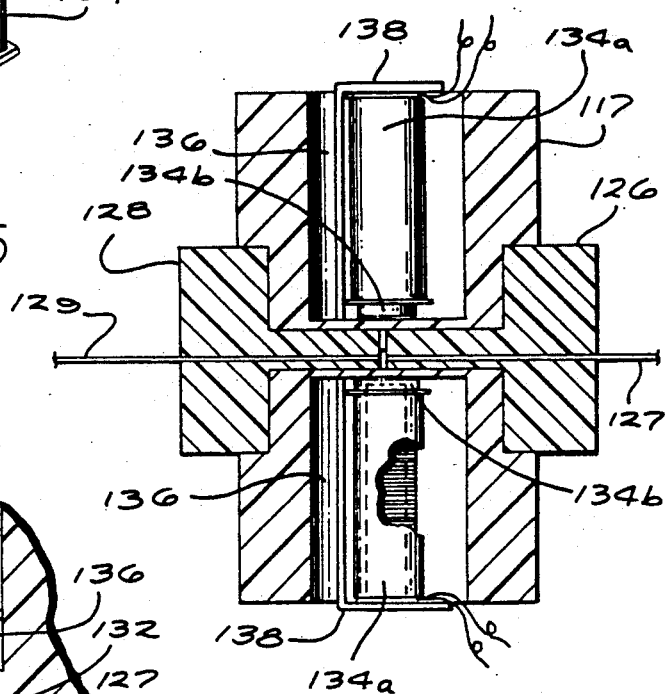
FIG. 5 is a sectional side view of the optical multiplexer of the present invention taken along the lines V—V in FIG. 4.
Figure 6:
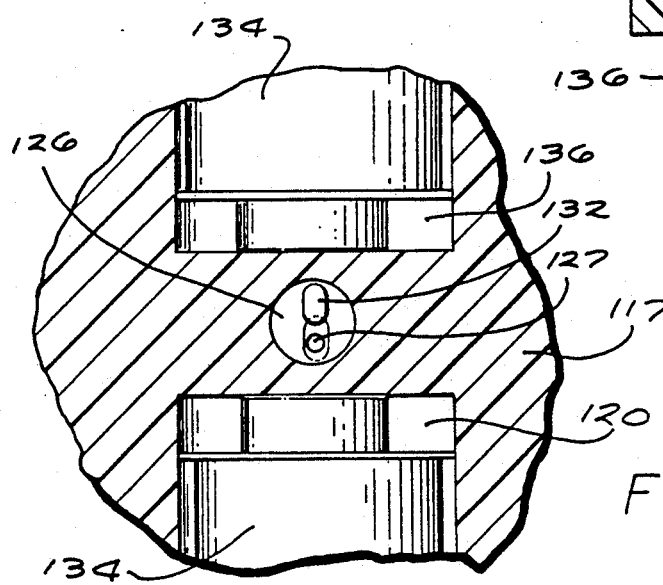
FIG. 6 is a sectional end view of the optical multiplexer of the present invention taken along the lines VI—VI in FIG. 4.

In use, the electromagnets 134 disposed about a particular bore 118 are energized so as to form a magnetic field within the bore, thus positioning the element 132 at an edge of the bore 118. As illustrated in FIG. 5, the input and output fiber optic cables 127 and 129 are respectively displaced from the central longitudinal axes of the ferrules 126 and 128. Thus, as illustrated in FIGS. 7 and 8, energization of the electromagnets 134 so as to form a field in a downward oriented direction would position the element 132 so as to block the optical path between the endfaces of the input and output fiber optic cables 127 and 129. Energization of the electromagnets 134 so as to form a field of reversed polarity, oriented upward, would displace the element 132 to the opposite side of the bore 118, thus permitting the passage of light from the input fiber optic cable 127 to the output fiber optic cable 129.

In a preferred embodiment of the optical multiplexer 114, the input and output fiber optic cables 127 and 129 are single-strand fiber optic waveguides. To minimize losses in light intensity through the optical multiplexer 114, the output fiber optic cable 129 preferably has a slightly larger diameter than the input fiber optic cable 127 so as to partially negate the effect of divergence at the endface of the input fiber optic cable 127. By way of example only, the input fiber optic cable could be provided with a core diameter of 500 microns while the output fiber optic cable 129 would preferably have a core diameter of 560 microns. Additionally the input fiber optic cables 127 may be provided with a smaller core diameter than the fiber optic cables employed to conduct light to the multiplexer 114. This reduced diameter can prevent lightly coupled higher order light modes from travelling through the multiplexer 114, thus reducing the noise level of the spectrophotometer 10. Referring to FIG. 1, for example, the fiber optic cables 35c, 37c and 67b, 68b could have a smaller core diameter than the fiber optic cables 35b, 37b and 67a, 68a.

The electromagnets 134 are preferably provided with magnetically conductive returns 138 which are attached to the ends 134a of the electromagnets 134 distant from the multiplexer bores 118. The returns 138 extend along the sides of the electromagnets 134 to the electromagnet ends 134b disposed close to the bores 118. The elements 132 disposed within the bores 118 and preferably, though not necessarily, have an ellipsoidal cross-section. This shape may be achieved by bonding together two circular pieces 132a and 132b as illustrated in FIG. 13A. The elements 132 may be composed of any suitable ferromagnetic material, preferably a hard material such as amorphous cobalt-iron. This composition has been found to retain its shape through several millions of optical cyclings between opened, light-transmitting, and closed, non-transmitting states of the multiplexer optical channels. In the embodiment illustrated in FIGS. 4–6 the ferrules 126 and 128 are typically some sort of thermoset compound. Preferably, the endfaces of the input and output ferrules 127 and 128 are polished to obtain an optimum light conduction through the endfaces of the fiber optic cables 27 and 129.

Figure 13:
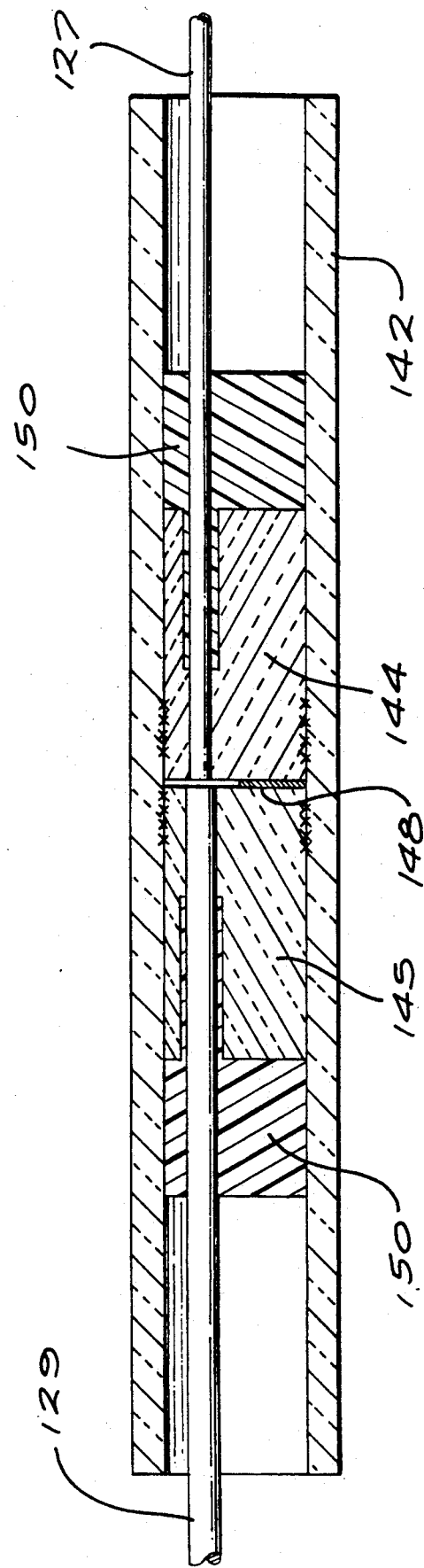
FIG. 13 is a side sectional view of another embodiment of the optical multiplexer of the present invention.
Figure 13A:
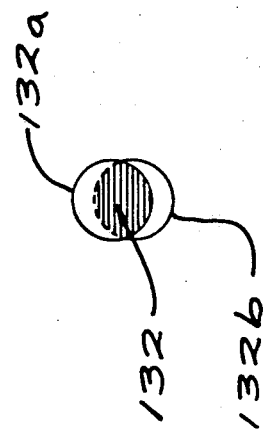
FIG. 13A is an end view of ferromagnetic element 132.

An alternative ferrule structure is illustrated in FIG. 13. This ferrule 140 includes a borosilicate tube 142 which is placed within the bores 118 of the multiplexer base 117. The input and output fiber optic cables 127 and 129 respectively terminate within plugs 144 and 145 located inside the tube 142. The plugs 144 and 145 are spaced apart so as to form a gap 148 within which the ferromagnetic element 132 is disposed and are fused to the tube 142 to provide a rigid and dust-free seal. Preferably some form of epoxy 150 is backfilled into the tube 142 to secure the fiber optic cables 127 and 129 within the respective plugs 144 and 145.

This embodiment enjoys certain advantages in that the plugs 144 and 145 are well secured with respect to the tube 142, assuring that variations in the spacing of the gap 148 are minimized, thus decreasing a potential source of optical noise. That is, variations in the light intensity throughput of the multiplexer 114.

Figure 9:
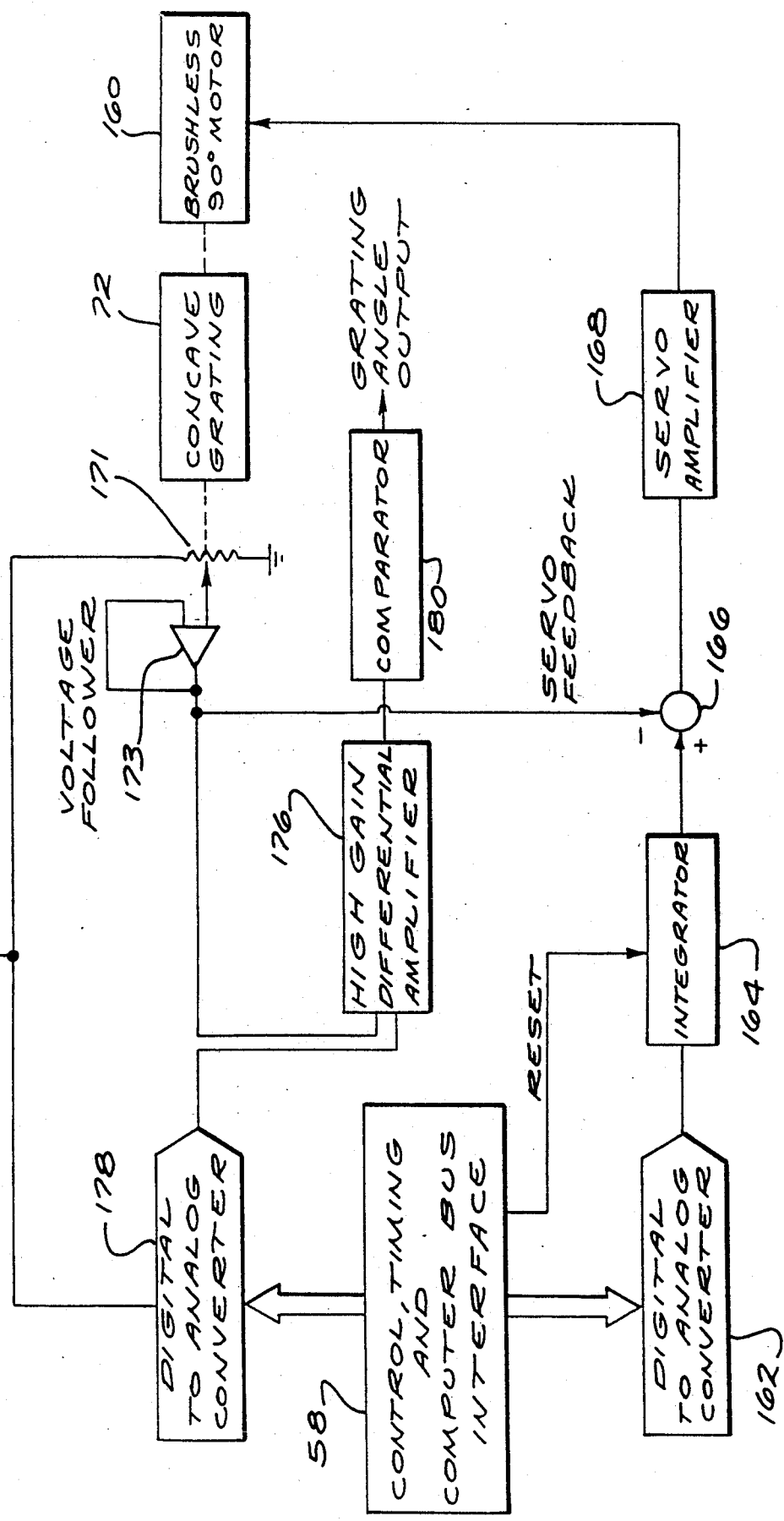
FIG. 9 is a schematic diagram of a generalized circuit of the present invention for driving a monochromator grating and measuring the angular orientation of the grating.

Referring to FIG. 9, there is shown one embodiment of an electronic circuit suitable for use as the grating drive 25 of the spectrophotometer 10 illustrated in FIG. 1. As shown in FIG. 9, the optical grating 22 is connected to a brushless motor 160. The brushless motor 60 is driven by the spectrophotometer control computer 58. Commands are sent from the computer 58 to the brushless motor 160 through a digital-to-analog converter 162 having its digital signal input coupled to the computer 58 and providing an analog output to an integrator circuit 164. The output of the integrator 164 is connected to one input of a summation network 166 which provides an output to a servo-amplifier 168 powering the motor 160. The opposing input to the summation network 166 is connected to a voltage follower 173 which provides an output corresponding to the output of an angular sensor 171. This angular sensor 171 in turn provides a signal corresponding to the angular orientation of the grating.

In operation, the computer 58 provides a signal to the integrator 164, through the digital-to-analog converter 162, which corresponds to an angular orientation rate of change for the grating. The output of the integrator 164 generates a voltage ramp of constant slope. A loop is thus provided between the output of the voltage follower 173, following the output of the grating angular orientation sensor 171, and the integrator 164 which causes the servo-amplifier 168 to drive the motor 160 at a generally constant rate.

Figure 10:
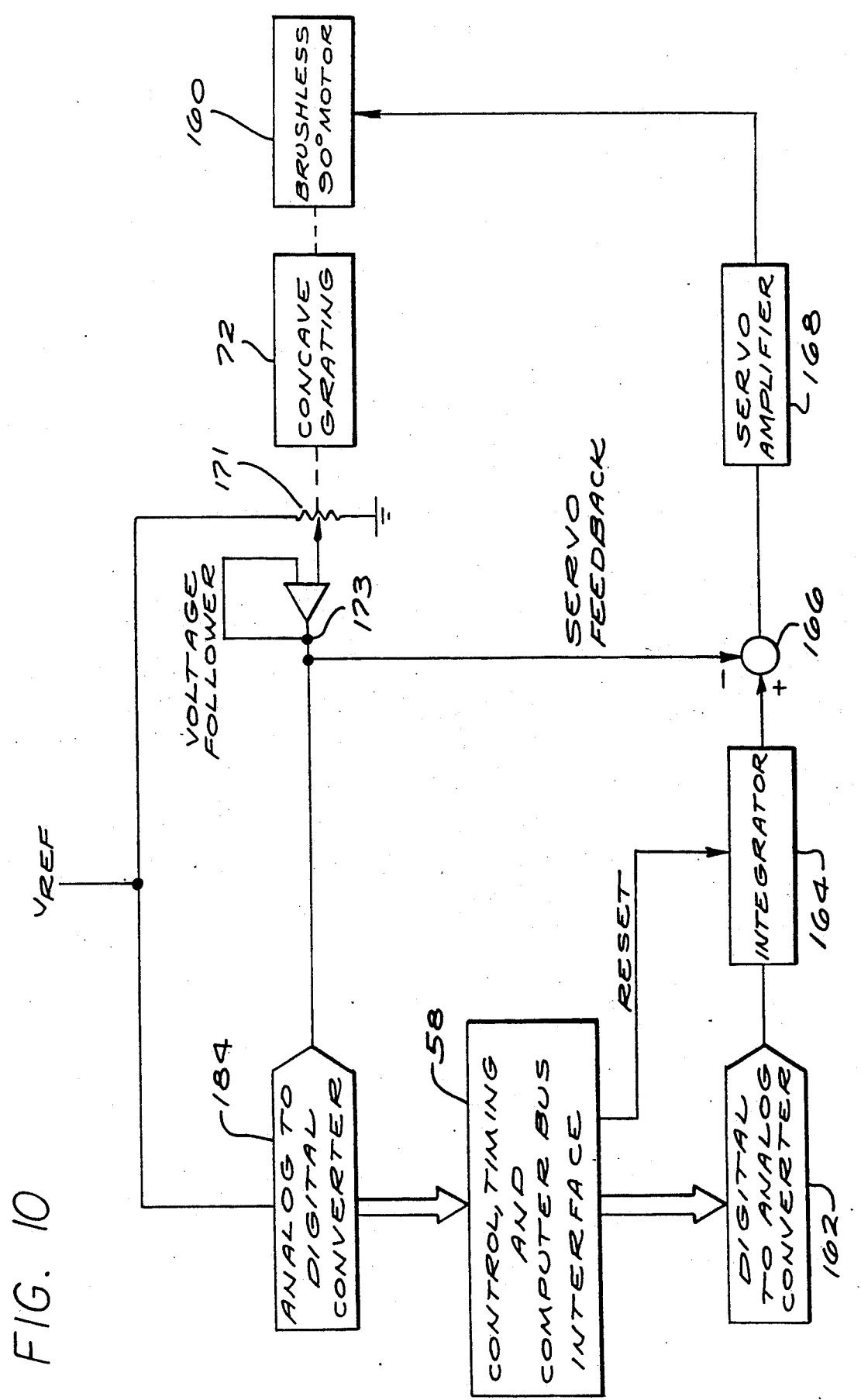
FIG. 10 is a schematic diagram of another embodiment of the electronic circuit for driving a grating monochromator and measuring the angular orientation of the grating.

The grating drive circuit shown in FIG. 10 further illustrates an embodiment of an electronic circuit suitable for sensing the precise angular orientation of the grating 22. In this circuit the output from the angular orientation sensor 171 is connected through a voltage follower 173 to one input of a high-gain differential amplifier 176. The computer 58 is connected to the second input of the high-gain differential amplifier 176 through a digital-to-analog converter 178. The output from the differential amplifier 176 is then connected to a comparator 180 which provides an output indicative of a particular grating angle orientation.

In use, the data stored in or calculated by the computer from the calibration of the grating drive which indicates some specific angular orientation of the grating 22 is sent through the analog-digital converter 178, to one input of the differential amplifier 176. When the grating angular orientation sensor 171 senses this orientation of the grating, the output of the differential amplifier 176 will approach and reach a minimum value, thus triggering the comparator 138. As the grating is swept by the motor 160 through an operational range of angular orientations, the control signals from the computer periodically change to indicate a new angular orientation which the grating 22 is approaching. In this manner, the comparator output 180 indicates to a high degree of precision when the concave grating 22 achieves a particular angular orientation.

In a preferred embodiment of the present inventive spectrophotometer, the angular orientation sensor 171 is a linear potentiometer including a highly linear conductive plastic potentiometer connected directly to a shaft that couples the grating 22 to the motor 160. This sensor provides a signal having a very precise linear relationship to the angular orientation of the grating which is highly repeatable.

Figure 11:
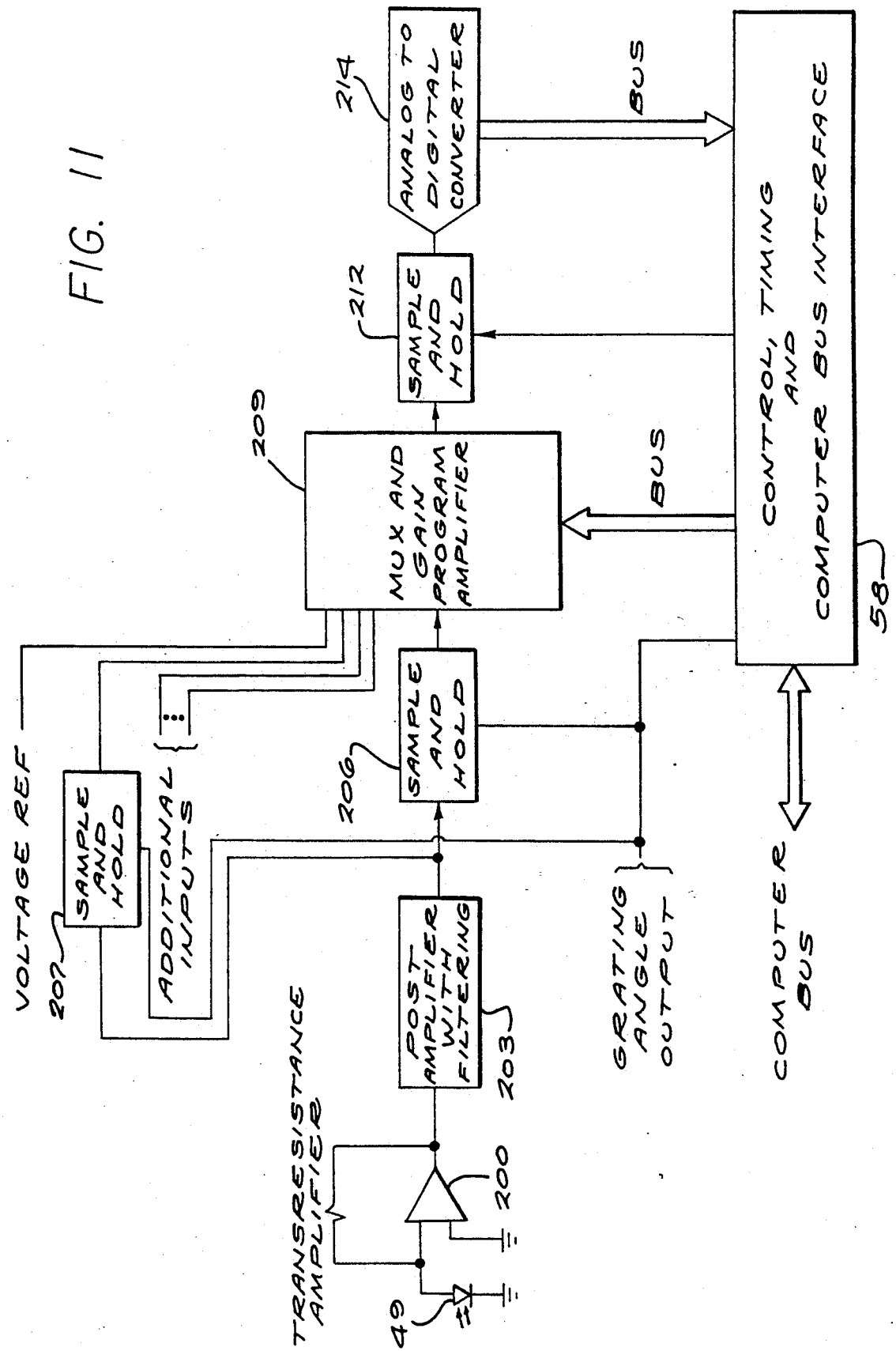
FIG. 11 is a schematic diagram of a preferred embodiment of an electronic circuit of the present invention for measuring the output voltage of a photodetector sensing the intensity of light conducted through the reference and sample fiber optic waveguides of the present invention.

An alternative angular sensing and drive circuit suitable for use with the spectrophotometer 10 is further illustrated in FIG. 11. In this circuit, the differential amplifier 176, digital-to-analog converter 178 and comparator 180 are replaced by a high-speed analog-to-digital converter 184 having an analog input coupled to the voltage follower 173 and providing a digitized signal to the computer 58. Using successive measurements from the high-speed analog-to-digital converter 184, the computer 58 internally compares data from the calibration scan with grating drive data from the converter 184 to estimate when light intensity signals from the photodetector 49 should be stored.

Referring to FIG. 11 there is shown an electronic circuit suitable for providing, conditioning and formatting of the voltage signals from the detectors 49 and 78 of the spectrophotometer 10 illustrated in FIG. 1. As shown, the conditioning circuit includes a transimpedance amplifier 200 integral with the detector 49 and having an output to a subsequent external amplifier 203 which preferably, though not necessarily, filters out some of the electronic noise from the transimpedance amplifier 200 and detector 49. The output from the external amplifier 203 is then connected to one or more sample-and-hold circuits 206 and 207 which have their outputs connected to an electronic multiplexer and programmable amplifier 209. The output from the multiplexer and programmable amplifier 209 is in turn connected to a second sample-and-hold circuit 212 having an output coupled to an analog-to-digital converter 214 having a digitized output to an interface bus which can be considered part of the computer 58.

In operation, the sample-and-hold circuits 206 and 207 continually sense the output from the external amplifier filter 203 until receipt of a hold command. This command can be provided either by the comparator circuit 180 from the grating orientation sensing circuit illustrated in FIG. 9 or, alternatively, upon receipt of a signal from the computer 58 when the computer is used for estimating the angular orientation of the grating, as in the circuit illustrated in FIG. 10.

While the sample-and-hold circuits 206 and 207 are still receiving a hold signal, the computer 58 provides a command signal to the multiplexer and programmable amplifier 209 designating which voltage signal from the sample-and-hold circuits 206 and 207 is to be transmitted to the second sample-and-hold circuit 212 and also designating the magnitude of gain to be provided by the amplifier 209. A hold command is then sent to the second sample-and-hold circuit 212, maintaining a constant level output signal from the second sample-and-hold circuit 212 for a sufficient time to permit the analog-to-digital converter 214 to digitize the analog output of the second sample-and-hold circuit 212 and allow the computer to access and store this information. After the amplified and digitized form of the output from one of the sample-and-hold circuits 206 or 207 has been stored by the computer 58, the hold signal to the second sample-and-hold circuit 212 is discontinued and a new command signal is sent to the multiplexer and programmable amplifier 209, designating the other of the sample-and-hold circuits 207 for transmission through the programmable amplifier with suitable amplification. Another hold signal is then sent to the second sample-and-hold circuit 212 for a sufficient time to permit subsequent digitization of this latter output.

In accordance with one methodology of the present invention, to provide an input to the analog-to-digital converter 214 which is within a preferred portion of the dynamic range of the converter 214 the computer 58 can be programmed to direct the programmable amplifier 209 to provide precisely the same gain to the voltage outputs of the sample-and-hold circuits 206 and 207 as they are alternatively transmitted through the amplifier 209. The subsequent digitized data from the alternative sample-and-hold circuits 206 and 207 are then averaged so as to advantageously minimize electronic noise generated by the conditioning circuit and the first sample-and-hold circuits 206 and 207. Alternatively, however, the data from the sample-and-hold circuits 206 and 207 can be employed to optimize the accuracy of the digitized output from the analog-to-digital converter 214 by commanding selective amplification from the programmable amplifier 209.

A presently preferred physical embodiment of the spectrophotometer discussed above is illustrated in FIG. 12. In this embodiment, all of the components of the spectrophotometer are housed in a single cabinet 250 while the sample chambers 61 and 64 are located some distance away. The cabinet 250 includes a front panel 252 slidable mounted on railings 254 so as to enable the front panel 252 to project out from the interior of the cabinet 250. In this illustration, various circuit boards 256 of the computer 58 are illustrated along with the monochromator light source 258, filter wheel 260 and grating drive 262. The optical interconnects 264 and 266 between fiber optic cables contained within the spectrophotometer and fiber optic cables disposed outside the spectrophotometer, leading to and from the sample chambers, are also mounted on the front panel 252 of the cabinet 250.

The present invention provides a highly accurate spectrophotometer suitable for a wide variety of applications requiring long-term stability and state-of-the-art accuracy. While only a few presently-preferred embodiments have been described in detail, it will be apparent to those familiar with the art that modifications to the presently-preferred embodiments of the spectrophotometer and spectrophotometric methodologies discussed above can be made without departing from the scope of the invention. For example, an additional column of referencing fiber optic cables could be employed in the optical input ferrule 80 illustrated in FIG. 3 to provide two columns of reference fiber optic cables on either side of the sampling column of fiber optic cables. This configuration would provide additional conditioning for short-term fluctuations in the intensity of the light output of the monochromator. Similarly, the number of sample chambers can be varied to include a considerably larger number of chambers or, alternatively, as few chambers as one. The reference fiber optic cables, such as cables 35 and 37 could also be of unitary construction and disposed entirely within the frame of the spectrophotometer. Consequently, the scope of the present invention should not be limited by the particular embodiments discussed above, but should be defined only by the claims set forth below and equivalents thereof.

What is claimed is:

1. A low noise spectrophotometer, comprising:
monochromater means for providing a light beam of variable wavelength at an output;
a first single strand fiber optic waveguide for conducting light from said monochromater means toward a sample;
a second single strand fiber optic waveguide for conducting light; and
translation means for alternatively positioning input ends of said first and second single strand fiber optic waveguides at the same position in space with respect to the output of said monochromater means, wherein said first and second fiber optic waveguides alternatively conduct light from said monochromater means to provide compensation for time and wavelength dependent fluctuations in the light intensity at the output of said monochromater means.

2. The low noise spectrophotometer of claim 1 further comprising:
a third single strand fiber optic waveguide for conducting light received from said sample; and
multiplexer means, optically coupled to output ends of said second and third single strand fiber optic waveguides, for alternatively conducting light from said second and third single strand fiber optic waveguides.

3. The low noise spectrophotometer of claim 2 further comprising detector means, optically coupled to an output of said multiplexer means, for producing an electric signal proportional to a sensed light intensity.

4. The low noise spectrophotometer of claim 3 further comprising fourth fiber optic means for conducting light from said multiplexer means to said detector means, wherein said fourth fiber optic means has a plurality of optical input ends.

5. The low noise spectrophotometer of claim 4 wherein said multiplexer means comprises:
a base having a first bore, extending through the base, with one end configured to receive an optical output end of said third fiber optic waveguides and an opposing end configured to receive one of the optical input ends of said fourth fiber optic means so as to form a gap within the bore, said base further having a second bore extending through the base with one end configured to receive an optical output end of said second fiber optic means and an opposing end configured to receive another of the optical input ends of said fourth fiber optic means so as to form a gap within the second bore;
first and second ferromagnetic elements respectively disposed within the gap in the first and second bores; and
first and second electromagnetic means for respectively forming magnetic fields within the gaps in the first and second bores, wherein magnetic fields of one polarity within the gaps in the first and second bores respectively position the first and second ferromagnetic elements so as to block light passage from said second and third fiber optic means to said fourth fiber optic means and magnetic fields of opposite polarity respectively position the first and second ferromagnetic elements so as to permit light passage.

6. The low noise spectrophotometer of claim 5 wherein the optical output ends of said second and third fiber optic waveguides include ferrules having end portions configured to respectively fit within the first and second bores of said multiplexer base with light conducting end faces of said second and third fiber optic waveguides respectively displaced from central longitudinal axes of the first and second bores.

7. The low noise spectrophotometer of claim 5 wherein said first and second electromagnetic means respectively include electromagnets disposed on opposite side of said first and second multiplexer bores.

8. The low noise spectrophotometer of claim 7 wherein the electromagnets of said first and second electromagnetic means respectively include ferromagnetic brackets, attached to first ends of said electromagnets, configured to extend towards and terminate adjacent opposing second ends of said electromagnets.

9. The low noise spectrophotometer of claim 5 wherein said first and second ferromagnetic elements are composed of amorphous cobalt-iron.

10. The low noise spectrophotometer of claim 5 wherein said first and second ferromagnetic elements have a generally ellipsoidal configuration.

11. The low noise spectrophotometer of claim 2 further comprising a first column of single strand fiber optic waveguides having optical input ends disposed adjacent said first single strand fiber optic waveguide and forming a line parallel to an exist slit of said monochromater means, a second column of single strand fiber optic waveguides having optical input ends disposed adjacent said first column of single strand fiber optic waveguide and forming a line parallel to said monochromater exit slit and said first column of waveguides, and a plurality of sample cells respectively coupled to said first column of single strand fiber optic waveguides.

12. The low noise spectrophotometer of claim 2 further comprising a short term referencing single strand fiber optic waveguide having an optical input and disposed adjacent said first single strand fiber optic waveguide on a side of first waveguide opposite said second single strand fiber optic waveguide.

13. The low noise spectrophotometer of claim 1 further comprising:
   third fiber optic waveguide for conducting light received from said sample;
   a short term intensity referencing single strand fiber optic waveguide having an optical input and disposed adjacent said first single strand fiber optic waveguide on a side of said first waveguide opposite said second single strand fiber optic waveguide;
   first detector means for producing an electrical signal proportional to a sensed light intensity;
   multiplexer means, optically coupled to said second single strand fiber optic waveguide and third fiber optic waveguide for alternatively conducting light to said first detector; and
   second detector means, optically coupled to said short term intensity referencing single strand fiber optic waveguide, for producing an electrical signal proportional to a sensed light intensity.

14. The low noise spectrophotometer of claim 11 wherein a plurality of single strand fiber optic waveguides of diameters smaller than the diameters of the single strand fiber optic waveguides of the first and second fiber optic column are disposed within interstices formed between the adjacent first and second columns of single strand fiber optic waveguides.

15. The low noise spectrophotometer of claim 1 wherein said translator means comprises:
   a base;
   a bracket connected to the optical inputs of said first and second fiber optic waveguides;
   slide means, having a first portion connected to the base and a second portion connected to the bracket, for permitting reciprocal motion between the first and second portions along a single axis; and
   displacement means for moving the slide means.

16. The low noise spectrophotometer of claim 1 wherein said monochromator means comprises:
   a grating;
   potentiometer means, coupled to said grating, for providing an output voltage signal indicative of the angular orientation of said grating;
   control means for selectively providing output voltage signals corresponding to the output signals of said potentiometer means;
   differential amplifier means, having a first input coupled to an output of said potentiometer means and a second input connected to an output of said control means, for providing an output voltage signal indicative of a voltage differential between said first and second inputs; and
   comparator means, having an input connected to an output of said differential amplifier means, for providing an output signal when the output of said differential amplifier means is zero, wherein said comparator means provides an output whenever the angular orientation of the grating matches an angle corresponding to an output signal selectively provided by said control means.

17. The low noise spectrophotometer of claim 3 further comprising electronic sensing means for sensing the output of said detector means, said electronic sensing means comprising:
   first sample and hold means for sampling the output voltage of the detector means and holding said voltage output on receipt of a command signal;
   programmed amplifier means for providing an output signal corresponding to a variable amplification of an output of said first sample and hold means upon receipt of a command signal;
   second sample and hold means for sampling the output of said programmed amplifier means and holding said output upon receipt of a command signal; and
   control means for providing command signals to set first and second sample and hold means and said programmed amplifier means, wherein the detector means output is stored in said first sample and hold means when the monochromator emits light at a desired wavelength and the output of said programmed amplifier means is stored in said second sample and hold for subsequent storing and processing.

18. The low noise spectrophotometer of claim 17 further comprising a plurality of third sample and hold means, electrically coupled to said detector means, for sampling the detector means output and storing said output upon receipt of a command signal, and wherein said programmed amplifier means further comprises multiplexer means for selectively connecting the plurality of third sample and hold means to the programmed amplifier means.

19. The low noise spectrophotometer of claim 1 further comprising:
   first detector means, optically coupled to the said second fiber optic waveguides, for producing an electrical signal proportional to a sensed light intensity;
   third fiber optic means for conducting light received from said sample; and
   second detector means, optically coupled to the said third fiber optic means, for producing an electrical signal proportional to a sensed light intensity.

20. A low noise spectrophotometer for studying the optical properties of a sample, comprising:
   monochromater means for producing monochromatic light of variable wavelength at an output;
   first single strand fiber optic waveguide conducting light from said monochromater means toward said sample;
   second single strand fiber optic waveguide conducting light;
   third single strand fiber optic waveguide conducting light received from said sample;

translation means for alternatively positioning optical input ends of said first and second fiber optic waveguides at the output of monochromater means;

multiplexer means for alternatively transmitting light conducted through said second and third fiber optic waveguides; and detector means, optically coupled to an output of said multiplexer means, for providing an electrical signal proportional to a sensed light intensity.

21. The low noise spectrophotometer of claim 20 wherein said multiplexer means comprises:

a base having a first and a second bore, each extending through the base and having opposing ends configured to receive optical ends of separate fiber optic waveguides means so as to form a gap within the bores;

first and second ferromagnetic elements respectively disposed within the gap in the first and second bores; and first and second electromagnetic means for respectively forming magnetic fields within the gaps in the first and second bores, wherein magnetic fields of one polarity within the gaps in the first and second bores respectively position the first and second ferromagnetic elements so as to block light passage through the respective bores and magnetic fields of opposite polarity respectively position the first and second ferromagnetic elements so as to permit light passage.

22. The low noise spectrophotometer of claim 21 wherein the optical output ends of said second and third single strand fiber optic waveguides include ferrules having end portions configured to respectively fit within the first and second bores of said multiplexer base with light conducting end faces of said second and third single strand fiber optic waveguides respectively displaced from central longitudinal axes of the first and second bores.

23. The low noise spectrophotometer of claim 21 wherein said first and second electromagnetic means respectively include electromagnets disposed on opposite side of said first and second multiplexer bores.

24. The low noise spectrophotometer of claim 21 wherein the electromagnets of said first and second electromagnetic means respectively include ferromagnetic brackets, attached to first ends of said electromagnets, configured to extend towards and terminate adjacent opposing second ends of said electromagnets.

25. The low noise spectrophotometer of claim 21 wherein said first and second ferromagnetic elements are composed of amorphous cobalt-iron.

26. The low noise spectrophotometer of claim 21 wherein said first and second ferromagnetic elements have a generally ellipsoidal configuration.

27. The low noise spectrophotometer of claim 20 wherein said translator means comprises:

a base;

a bracket connected to the optical inputs of said first and second single strand fiber optic waveguides;

slide means, having a first portion connected to the base and a second portion connected to the bracket, for permitting reciprocal motion between the first and second portions along a single axis; and displacement means for moving the slide means.

28. The low noise spectrophotometer of claim 27 wherein said displacement means comprises an electromagnet coupled to the base and a ferromagnetic element coupled to the bracket.

29. The low noise spectrophotometer of claim 28 wherein the bracket forms an aperture and wherein said displacement means includes a screw, having a conic shaped end, threadingly engaging the base so that the conic end engages the bracket aperture, wherein displacement of the screw with respect to the base varies a travel distance of the bracket and the slide means second portion.

30. The low noise spectrophotometer of claim 28 wherein said monochromator means comprises:

a grating;

potentiometer means, coupled to said grating, for providing an output voltage signal indicative of the angular orientation of said grating;

control means for selectively providing output voltages signals corresponding to potentiometer means output signals;

differential amplifier means, having a first input coupled to an output of said potentiometer means and a second input connected to an output of said control means, for providing an output voltage signal indicative of a voltage differential between said first and second inputs; and comparator means, having an input connected to an output of said differential amplifier means, for providing an output signal when the output of said differential amplifier means is zero, wherein said comparator means provides an output whenever the angular orientation of the grating matches an angle corresponding to an output signal selectively provided by said control means.

31. The low noise spectrophotometer of claim 28 further comprising an electronic sensing means for storing the output of the detector means, said sensing means comprising:

first sample and hold means for sampling the output voltage of the detector means and holding said voltage output on receipt of a command signal;

programmed amplifier means for providing an output signal corresponding to a variable amplification of an output of said first sample and hold means upon receipt of a command signal;

second sample and hold means for sampling the output of said programmed amplifier means and holding said output upon receipt of a command signal; and control means for providing command signals to set first and second sample and hold means and said programmed amplifier means, wherein the detector means output is stored in said first sample and hold means when the monochromator emits light at a desired wavelength and the output of said programmed amplifier means sample and hold is stored in said second sample and hold for subsequent storing and processing.

32. The low noise spectrophotometer of claim 20 further comprising:

a short-term referencing single strand fiber optic waveguide having an optical input end coupled to said translator adjacent said first and second single strand fiber optic waveguides and on a side of said first single strand fiber optic waveguide opposite said second single strand fiber optic waveguide; and second detector means, optically coupled to an output of said short-term referencing single strand fiber optic waveguide, for providing an electrical signal proportional to a sensed light intensity.

33. The low noise spectrophotometer of claim 20 wherein said multiplexer means comprises:
a base having a plurality of bores;
a plurality of tubes respectively disposed within said bores;
a plurality of first plugs, respectively disposed within said tubes, each configured to receive a first single strand fiber optic waveguide;
a plurality of second plugs, respectively disposed within said tubes opposite first plugs so as to form gaps, each second plug configured to receive a second single strand fiber optic waveguide;
a plurality of ferromagnetic elements respectively disposed within said gaps between a corresponding pair of first and second plugs; and
a plurality of electromagnetic means for respectively forming independent electromagnetic fields within said gaps, wherein a magnetic field of a first polarity within a gap positions a corresponding ferromagnetic element within the gap so as to allow light passage between a pair of first and second plugs and a magnetic field of a second reversed polarity within a gap positions a corresponding ferromagnetic element within the gap so as to block light passage between the pair of first and second plugs.

34. The low noise spectrophotometer of claim 32 wherein said first and second plugs respectively form apertures therethrough, said apertures each having a first diameter portion communicating with one end face of said respective first and second plugs and a second diameter portion communicating with another opposing end face of said respective first and second plugs.

35. The low noise spectrophotometer of claim 33 wherein said first and second plugs respectively form apertures there through positioned off-center from a longitudinal axis of the respective first and second plugs.

36. The low noise spectrophotometer of claim 33 wherein said electromagnetic means comprises a plurality of electromagnet pairs respectively disposed on opposing sides of said bores, each electromagnet having a ferromagnetic bracket attached to a first end of said electromagnet, extending towards and terminating adjacent an opposing second end of said electromagnet.

37. The low noise spectrophotometer of claim 33 wherein said ferromagnetic elements are composed of amorphous cobalt-iron.

38. A low noise spectrophotometer for studying the optical properties of a sample, comprising:
monochromater means for producing monochromatic light of variable wavelength at an output;
first single strand fiber optic waveguide for conducting light to said sample;
second single strand fiber optic waveguide for conducting light;
translation means for alternatively positioning optical input ends of said first and second single strand fiber optic waveguides at the same point with respect to the output of said monochromater means;
third single strand fiber optic waveguide for conducting light received from said sample;
first detector means, optically coupled to an output of said second fiber optic means, for producing an electrical signal proportional to a sensed light intensity; and
second detector means, optically coupled to an output of said third fiber optic waveguide, for providing an electric signal proportional to a sensed intensity.

39. The low noise spectrophotometer of claim 38 wherein said translation means comprises:
a base;
a bracket connected to the optical inputs of said first and second fiber optic waveguides;
slide means, having a first portion connected to the base and a second portion connected to the bracket, for permitting reciprocal motion between the first and second portions along a single axis; and
displacement means for moving the slide means.

40. The low noise spectrophotometer of claim 38 wherein said monochromator means comprises:
a grating;
potentiometer means, coupled to said grating, for providing an output voltage signal indicative of the angular orientation of said grating;
control means for selectively providing voltage signals corresponding to potentiometer means output signals of said potentiometer means;
differential amplifier means, having a first input coupled to an output of said potentiometer means and a second input connected to an output of said control means, for providing an output voltage signal indicative of a voltage differential between said first and second inputs; and
comparator means, having an input connected to an output of said differential amplifier means, for providing an output signal when the output of said differential amplifier means is zero, wherein said comparator means provides an output whenever the angular orientation of the grating matches an angle corresponding to an output signal selectively provided by said control means.

41. The low noise spectrophotometer of claim 38 further comprising electronic sensing means for sensing the electrical signal output of either of said detector means, the sensing means comprising:
first sample and hold means for sampling the output voltage of either detector means and holding said voltage output on receipt of a command signal;
programmed amplifier means for providing an output signal corresponding to a variable amplification of an output of said first sample and hold means upon receipt of a command signal;
second sample and hold means for sampling the output of said programmed amplifier means and holding said output upon receipt of a command signal; and
control means for providing command signals to set first and second sample and hold means and said programmed amplifier means, wherein an output from either detector means is stored in said first sample and hold means when the monochromater emits light at a desired wavelength and the output of said programmed amplifier means sample and hold is stored in said second sample and hold for subsequent storing and processing.

42. The low noise spectrophotometer of claim 38 further comprising a referencing single strand fiber optic waveguide having an optical input end disposed adjacent an optical input end of said first single strand fiber optic waveguide, and further comprising first multiplexing means for alternatively transmitting light from the second fiber optic means single strand fiber optic waveguide to said first detector.

43. The low noise spectrophotometer of claim 38 wherein said first, second and third fiber optic waveguides are respectively a plurality of single strand fiber optic waveguides and wherein optical input ends of the respective single strand fiber optic waveguides of the first and second fiber optic means are attached to the translator adjacent one another in columns oriented parallel to an exit slit of the monochromater, and further comprising:
   a plurality of sample cells respectively optically coupled to output ends of the plurality of single strand fiber optic waveguides of the first fiber optic means and further optically coupled to input ends of the respective plurality of single strand fiber optic waveguides of the third fiber optic means;
   first multiplexer means for alternatively transmitting light to said first detector means from the plurality of single strand fiber optic waveguides of the second fiber optic waveguides; and
   second multiplexer means for alternatively transmitting light to said second detector means from any of the plurality of single strand fiber optic waveguides of the third fiber optic means.

44. A low noise spectrophotometer of claim 43 wherein said first and second multiplexer means respectively comprise:
   a base having a plurality of bores extending there through, each bore having opposing ends respectively configured to receive a single strand fiber optic waveguide so as to form a gap inside the bore;
   a plurality of ferromagnetic elements respectively disposed within the gaps inside the bores; and
   a plurality of electromagnetic means for respectively forming magnetic fields within the gaps inside the bores, wherein magnetic fields of one plurality within the gaps respectively position the ferromagnetic elements so as to block light passage through the respective bores and magnetic fields of opposite plurality respectively positioned the ferromagnetic elements so as to permit light passage through the bores.

45. The low noise spectrophotometer of claim 43 wherein said first and second multiplexer means respectively comprise:
   a base having a plurality of bores projecting there through;
   a plurality of tubes respectively disposed within the bores;
   a plurality of first plugs, respectively disposed within the tubes, each configured to receive a single strand fiber optic waveguide;
   a plurality of second plugs, respectively disposed within the tubes, opposite the first plugs so as to form gaps, each second plug configured to receive a single strand fiber optic waveguide;
   a plurality of ferromagnetic elements, respectively disposed inside said gaps; and
   a plurality of electromagnetic means for respectively forming reversible electromagnetic fields within said gaps, wherein fields of a first plurality position the ferromagnetic elements so as to allow light through said respective gaps and fields of a second reverse plurality position the respective ferromagnetic elements within said gaps to block light passage.

46. A spectrophotographic method to at least partially compensate anomalies within a spectrophotographic apparatus, said method employing a spectrophotographic apparatus having a monochromater, a first single strand fiber optic waveguide for directing light from an output of the monochromater to a sample, a second single strand fiber optic waveguide for directing light from the monochromater output and a translator for alternatively positioning optical inputs of the first and second fiber optic waveguides at the same predetermined location with respect to the monochromater output, the steps of said method comprising:
   scanning the wavelength of the light from the monochromater with the optical input of one of said fiber optic waveguides at said predetermined location; and
   positioning the optical input of the other of said fiber optic waveguides at the same predetermined location and again scanning the wavelength of the light from the monochromater, wherein light intensity data from the separate scans can be used for anomaly compensation.

47. The method of claim 46 further comprising the step of monitoring the output of the second fiber optic waveguide during while the wavelength of light from the monochromater is being scanned with the optical input of the first fiber optic waveguide positioned at said predetermined location.

48. An optical multiplexer, comprising:
   a base having a plurality of bores;
   a plurality of tubes respectively disposed within said bores;
   a plurality of first plugs, respectively disposed within said tubes, each configured to receive a first single strand fiber optic waveguide;
   a plurality of second plugs, respectively disposed within said tubes opposite first plugs so as to form gaps, each second plug configured to receive a second single strand fiber optic waveguide;
   a plurality of ferromagnetic elements respectively disposed within said gaps between a corresponding pair of first and second plugs; and
   a plurality of electromagnetic means for respectively forming independent electromagnetic fields within said gaps, wherein a magnetic field of a first polarity within a gap positions a corresponding ferromagnetic element within the gap so as to allow light passage between a pair of first and second plugs and a magnetic field of a second reversed polarity within a gap positions a corresponding ferromagnetic element within the gap so as to block light passage between the pair of first and second plugs.

49. The optical multiplexer of claim 48 wherein said electromagnetic means comprises a plurality of electromagnet pairs respectively disposed on opposing sides of said bores, each electromagnetic having a ferromagnetic bracket attached to a first end of said electromagnet, extending towards and terminating adjacent an opposing second end of said electromagnet.

50. The optical multiplexer of claim 48 wherein said ferromagnetic elements are composed of amorphous cobalt-iron.

51. The optical multiplexer of claim 48 wherein said first and second plugs respectively form apertures there through positioned off-center from a longitudinal axis of the respective first and second plugs.

* * * * *